(12) United States Patent
Gaines

(10) Patent No.: US 9,068,739 B2
(45) Date of Patent: Jun. 30, 2015

(54) DECORATIVE FRAGRANCE DIFFUSER HAVING A LIGHT SOURCE MOUNTED TO A BASE AND A SPACE FOR CUSTOM INSERTS

(71) Applicant: THE GAINES GROUP, Houston, TX (US)

(72) Inventor: Tom Gaines, Sugar Land, TX (US)

(73) Assignee: THE GAINES GROUP, Houston, TX (US)

( * ) Notice: Subject to any disclaimer, the term of this patent is extended or adjusted under 35 U.S.C. 154(b) by 0 days.

(21) Appl. No.: 13/957,571

(22) Filed: Aug. 2, 2013

(65) Prior Publication Data
US 2014/0036475 A1  Feb. 6, 2014

Related U.S. Application Data

(60) Provisional application No. 61/678,847, filed on Aug. 2, 2012.

(51) Int. Cl.
*F21V 33/00* (2006.01)
*A61L 9/03* (2006.01)

(52) U.S. Cl.
CPC ....... *F21V 33/0032* (2013.01); *Y10T 29/49826* (2015.01); *A61L 9/03* (2013.01); *A61L 2209/12* (2013.01); *A61L 2209/135* (2013.01)

(58) Field of Classification Search
CPC .......... G02F 1/133603; F21V 33/0032; H05B 33/00; A47G 1/0622
USPC ............. 392/394, 390, 386, 393; 362/96
See application file for complete search history.

(56) References Cited

U.S. PATENT DOCUMENTS

| 4,647,428 | A * | 3/1987 | Gyulay | 422/4 |
|---|---|---|---|---|
| 8,494,351 | B1 * | 7/2013 | Hayes | 392/393 |
| 2005/0144818 | A1 * | 7/2005 | Zilberman | 40/306 |
| 2007/0008730 | A1 * | 1/2007 | Hsieh | 362/382 |
| 2008/0302792 | A1 * | 12/2008 | Puckett | 220/62.21 |
| 2010/0097814 | A1 * | 4/2010 | Lederer | 362/392 |
| 2012/0318780 | A1 * | 12/2012 | Juarez | 219/209 |

* cited by examiner

*Primary Examiner* — Tracie Y Green
(74) *Attorney, Agent, or Firm* — Patterson & Sheridan, LLP

(57) ABSTRACT

The present disclosure generally relates to a decorative fragrance diffuser and methods of use thereof. The decorative fragrance diffuser may be comprised of a base and a light source mounted to the base. The decorative fragrance diffuser may further comprise an inner glass surrounding the light source and an interchangeable outer glass surrounding the inner glass, whereby an annular area is formed between the inner and outer glass. The decorative fragrance diffuser may further comprise a custom insert located between the inner glass and the outer glass. The decorative fragrance diffuser may further comprise a top disposed above the inner glass, the top including a basin for holding a fragrant element. The method of using the decorative fragrance diffuser may comprise following instructions or a template to create the custom insert with suitable dimensions.

16 Claims, 8 Drawing Sheets

DECORATIVE FRAGRANCE DIFFUSER HAVING A LIGHT SOURCE MOUNTED TO A BASE AND A SPACE FOR CUSTOM INSERTS

BACKGROUND OF THE INVENTION

1. Field of the Invention

Embodiments of the present invention generally relate to a decorative fragrance diffuser.

2. Summary of the Invention

The present invention generally relates to a decorative fragrance diffuser. The decorative fragrance diffuser may be comprised of a base and a light source mounted to the base. The decorative fragrance diffuser may further comprise an inner glass surrounding the light source and an outer glass surrounding the inner glass. The decorative fragrance diffuser may further comprise a custom insert located between the inner glass and the outer glass. The decorative fragrance diffuser may further comprise a top disposed above the inner glass, the top including a basin for holding a fragrant element.

The present invention also generally relates to a method of using a decorative fragrance diffuser. The method may be comprised of providing a base and a light source mounted to the base. The method may further comprise surrounding the light source with an inner glass resting on the base and surrounding the inner glass with an outer glass resting on the base. An annular area is formed between the inner and outer glass. The method may further comprise creating a custom insert configured to be placed in the annular area between the inner glass and the outer glass and placing the custom insert in the annular area. The method may further comprise heating a fragrant element with heat from the light source. The step of creating the custom insert may further comprise following instructions or a template to create the custom insert with suitable dimensions.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

The present disclosure includes a fragrance diffuser 100 and methods for using the fragrance diffuser 100. Aspects of the present disclosure provide for a readily customizable assembly with which a user can readily illuminate a personalized item, such as photographs or artwork, in an attractive fragrance diffuser.

Figure 1:
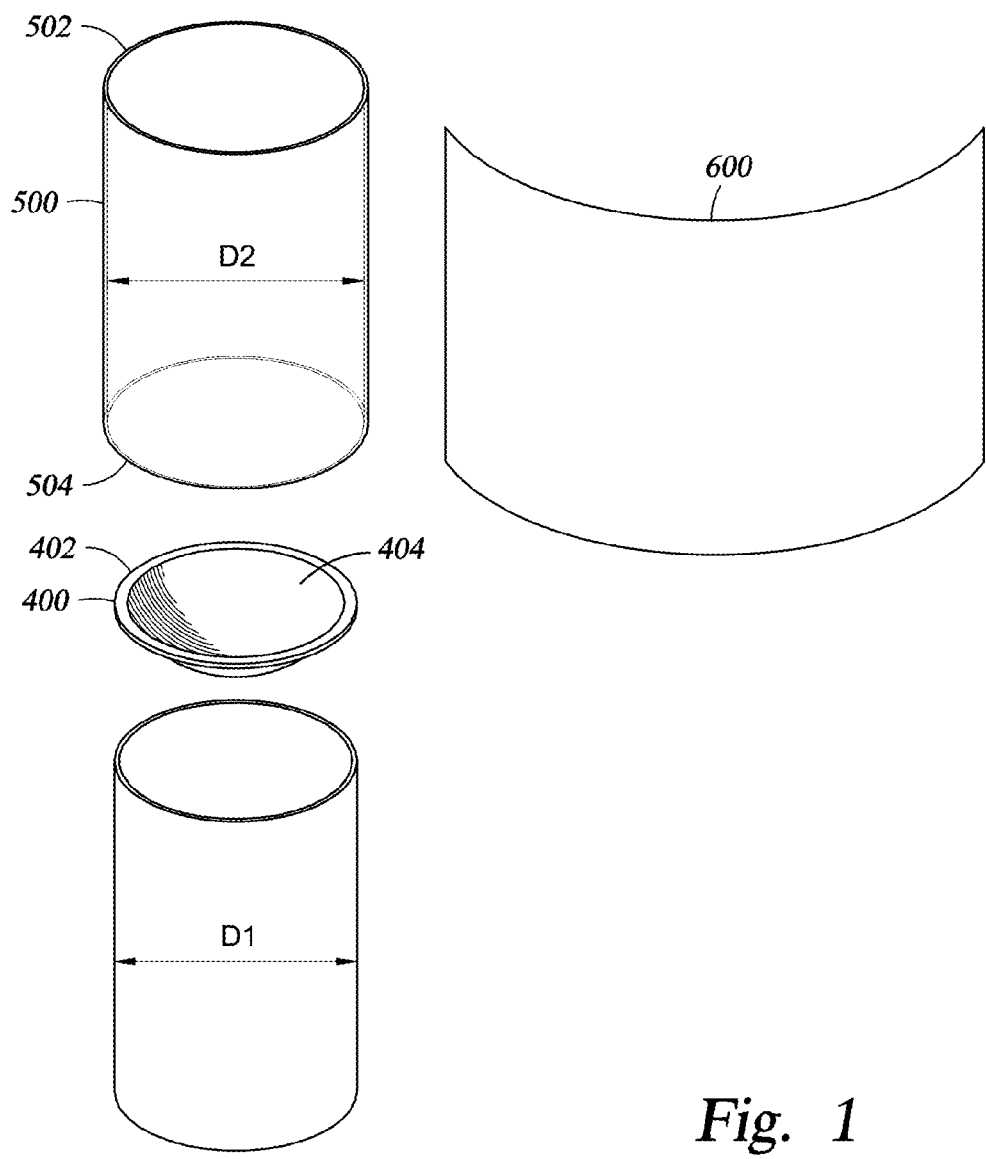
FIG. 1 is a perspective view of various components of a fragrance diffuser.
Figure 1:
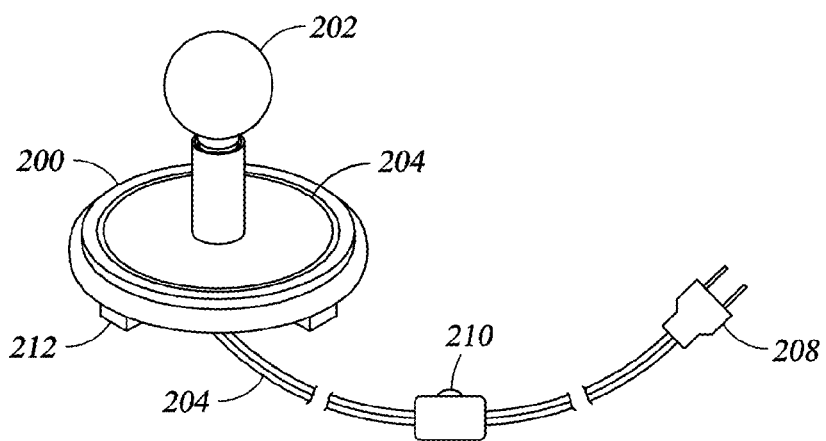

In FIG. 1, the components of fragrance diffuser 100 are shown. The fragrance diffuser includes a base 200 with a light source 202. The light source 202 may be an incandescent bulb. Other types of light sources are well known in the art and may also be used in the fragrance diffuser 100. Other possible light sources may include, but are not limited to, an LED light source, a fluorescent light source, a wax candle, etc. As discussed further below, in some embodiments, the light source 200 may be an incandescent bulb which can heat a fragrant element.

For some embodiments in which the light source 202 requires electricity, the base 200 may include an electrical cord 206 with a plug 208. The electrical cord may also include a switch 210. The switch 210 may be any suitable switch known in the art. In the embodiment shown, the switch 210 is shown on the electrical cord 206. However, the switch 210 may be located elsewhere, such as on the round portion of the base 200. In other embodiments in which the light source 202 requires electricity, the base 200 may include a battery compartment so that one or more batteries can be provided to provide electricity to the light source 202.

Figure 2:
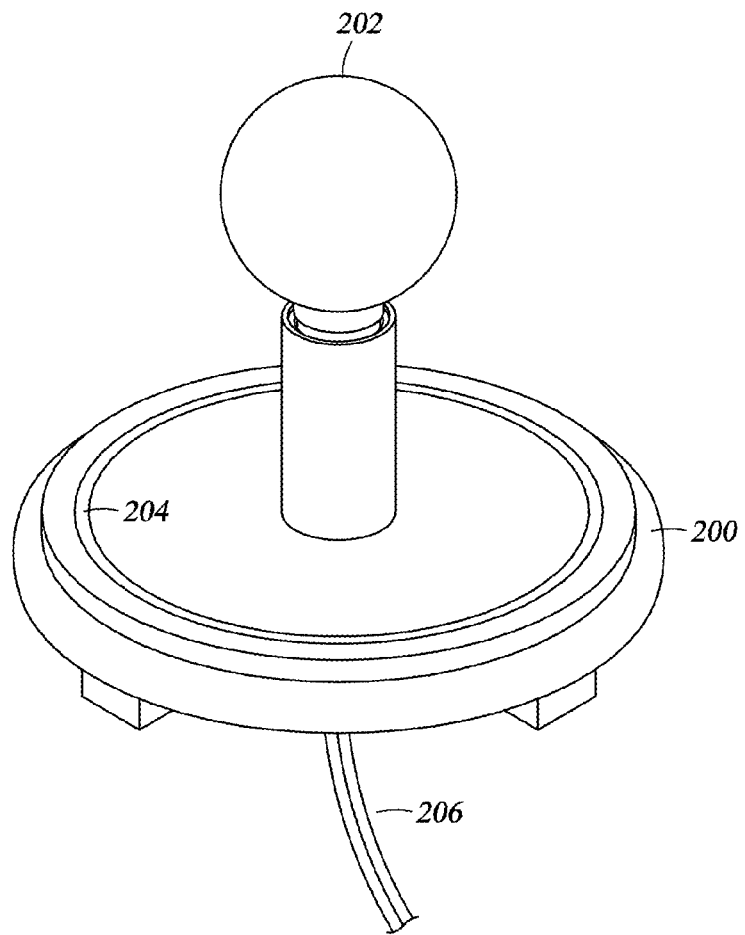
FIG. 2 is a perspective view of aspects of the fragrance diffuser.
Figure 3:
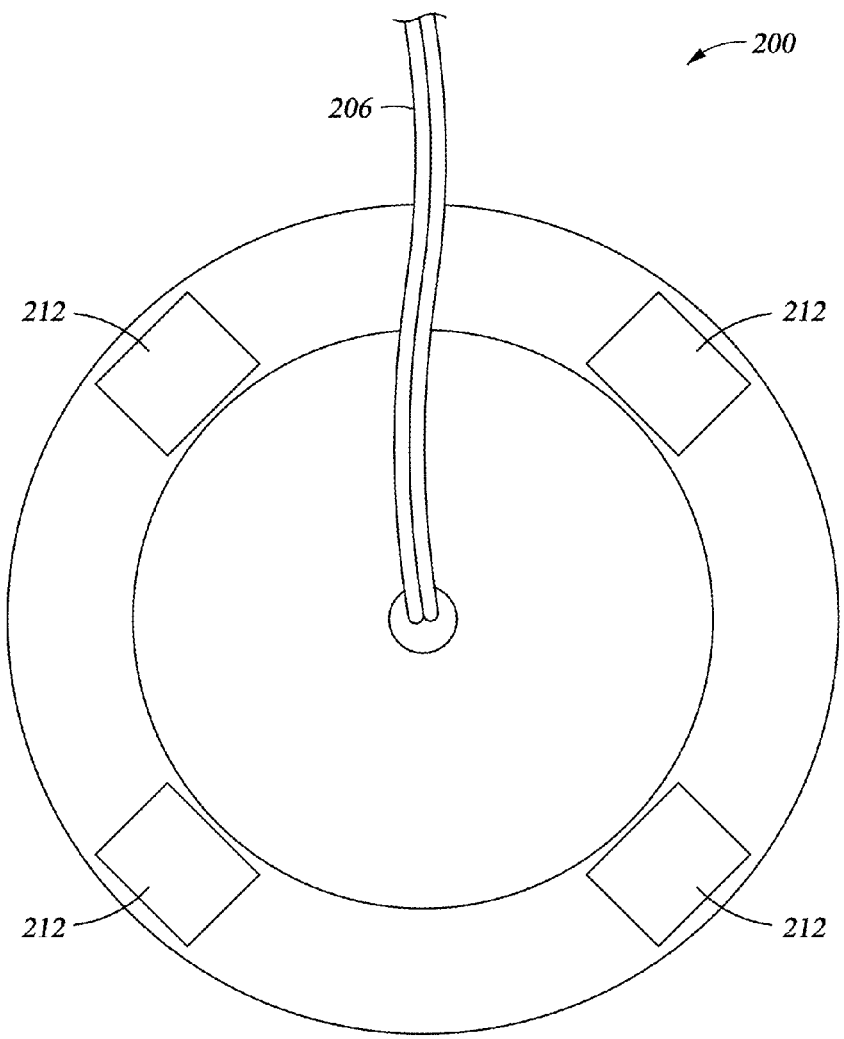
FIG. 3 is a bottom view of aspects of the fragrance diffuser.

The base 200 also includes a groove 204. The groove 204 is configured to receive a bottom edge 304 of an inner glass 300, as discussed further below. The base 200 also includes supports 212. The supports 212 may be feet or legs that support the base 200 on any suitable surface where the user intends to locate the fragrance diffuser 100. FIG. 2 illustrates a perspective view of the base 200 with light source 202. FIG. 3 illustrates a bottom view of the base 200, showing supports 212.

Figure 4:
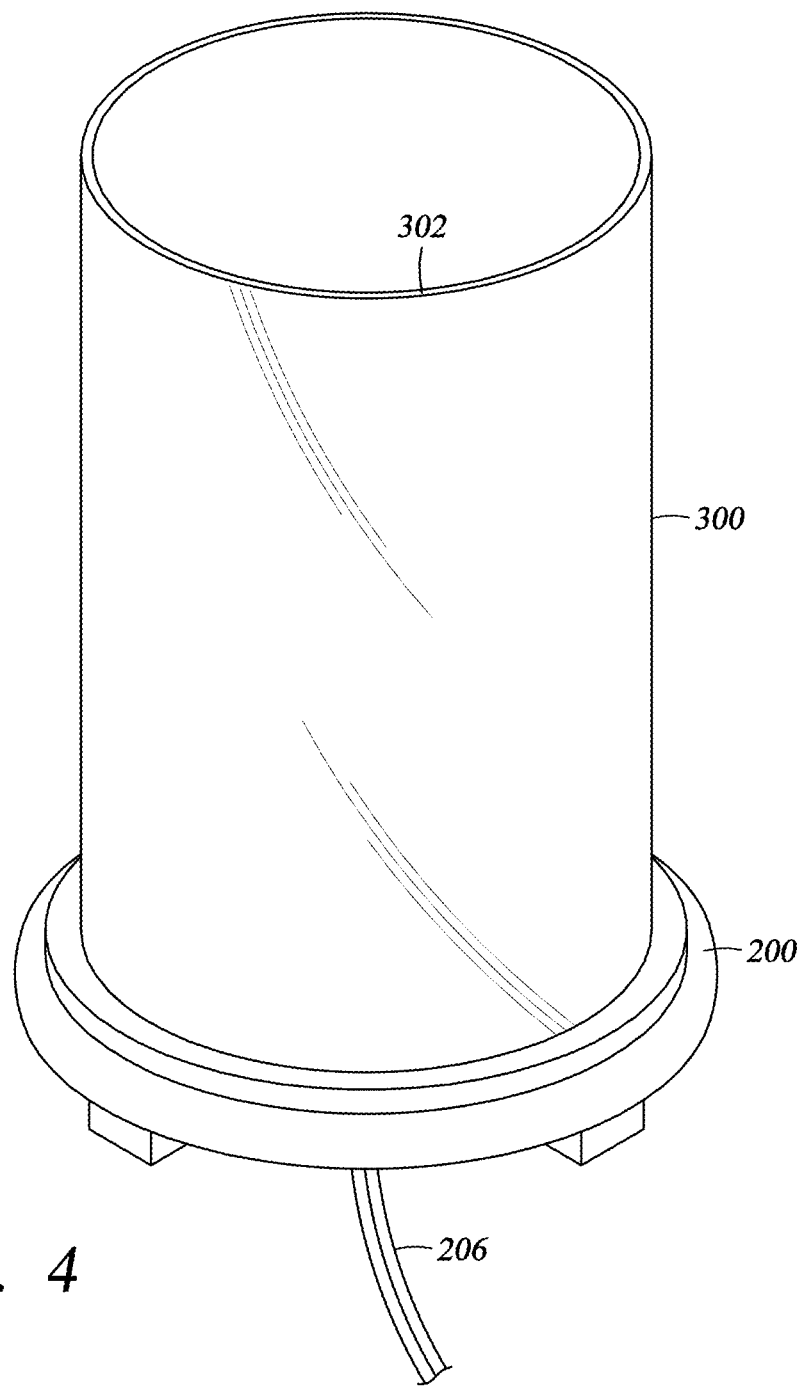
FIG. 4 is a perspective view of aspects of the fragrance diffuser.

The fragrance diffuser 100 also includes the inner glass 300. The inner glass 300 includes a top edge 302 and the bottom edge 304. The inner glass 300 may be a cylinder, as shown in the illustrated embodiment, although other shapes may be used without departing from the present disclosure. For example, the inner glass 300 may have an octagon or other polygonal shape when viewed from the top edge 302 or bottom edge 304. As noted, the groove 204 in the base 200 has a shape suitable to receive the bottom edge 304 of the inner glass 300. For embodiments in which the inner glass 300 is a cylinder, the top edge 302 and the bottom edge 304 each have a diameter $D_1$, and the groove 204 also has a matching diameter $D_1$. For embodiments in which the inner glass 300 is a shape other than a cylinder, the bottom edge 304 and the groove 204 have appropriately matching geometries for the groove 204 to receive the bottom edge 304. FIG. 4 illustrates the base 200 with the inner glass 300 positioned with the groove 204 receiving the bottom edge 304.

The inner glass 300 may be made of glass. However, other suitable materials, such as polycarbonate, may be used. The inner glass 300 may be opaque to diffuse light from the light source 202. In some embodiments, the inner glass 300 may be transparent, i.e., not opaque. In other embodiments, the inner glass 300 may be colored or textured to add a desired illumination effect to light from the light source 202.

Figure 5:
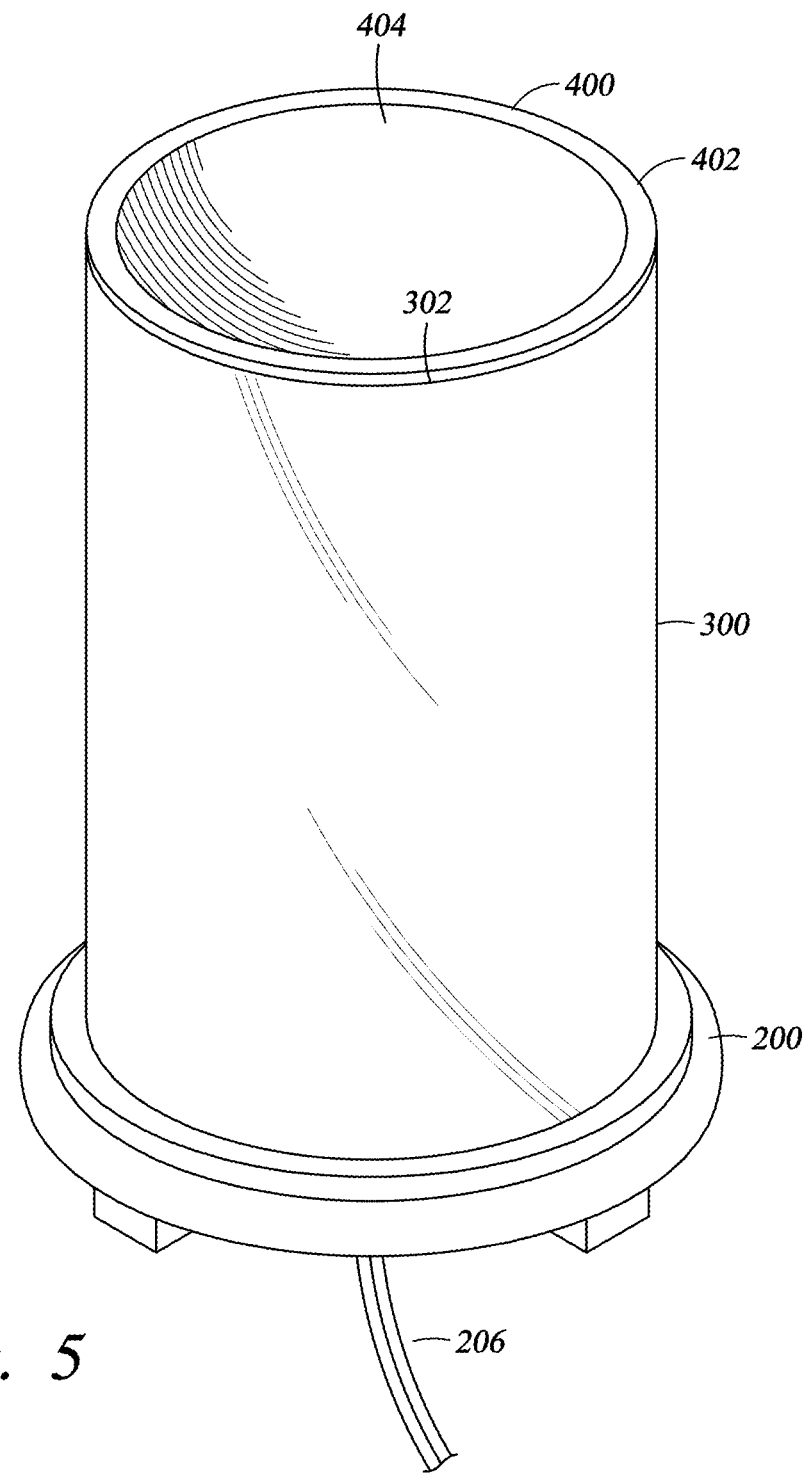
FIG. 5 is a perspective view of aspects of the fragrance diffuser.

The fragrance diffuser 100 may include cover 400. The cover 400 may be made of glass or other suitable material. In some embodiments, the cover 400 may be made of the same material as the inner glass 300. The cover 400 may include a support edge 402 configured to rest on the top edge 302 of the inner glass 300. The support edge 402 and the top edge 302 may have suitable matching geometries. For example, in embodiments in which the inner glass 300 is a cylinder, the top edge 302 and the support edge 402 may each have matching diameters $D_1$. In some embodiments, the perimeter of the cover 400 may have a geometry different from that of the top edge 302 of the inner glass 300, so long as one or more portions of the top edge 302 of the inner glass 300 support the cover 400. FIG. 5 illustrates the base 200 with the top edge 302 supporting the support edge 402.

The cover 400 may include a concave basin portion 404. The basin portion 404 is configured to support fragrant elements, such as scented wax particles. When the base 200 is provided with an incandescent bulb as the light source 202, the heat from the light source 202 causes the fragrant element to emit and diffuse a pleasing aroma. A user can use a different fragrant element for different aromas.

The fragrance diffuser 100 also includes outer glass 500. The outer glass may be made of glass or other suitable material. The outer glass 500 may be transparent. In some embodiments, the outer glass 500 may include texture or other decorative elements to add a desired decorative effect to the fragrance diffuser 100.

Figure 6:
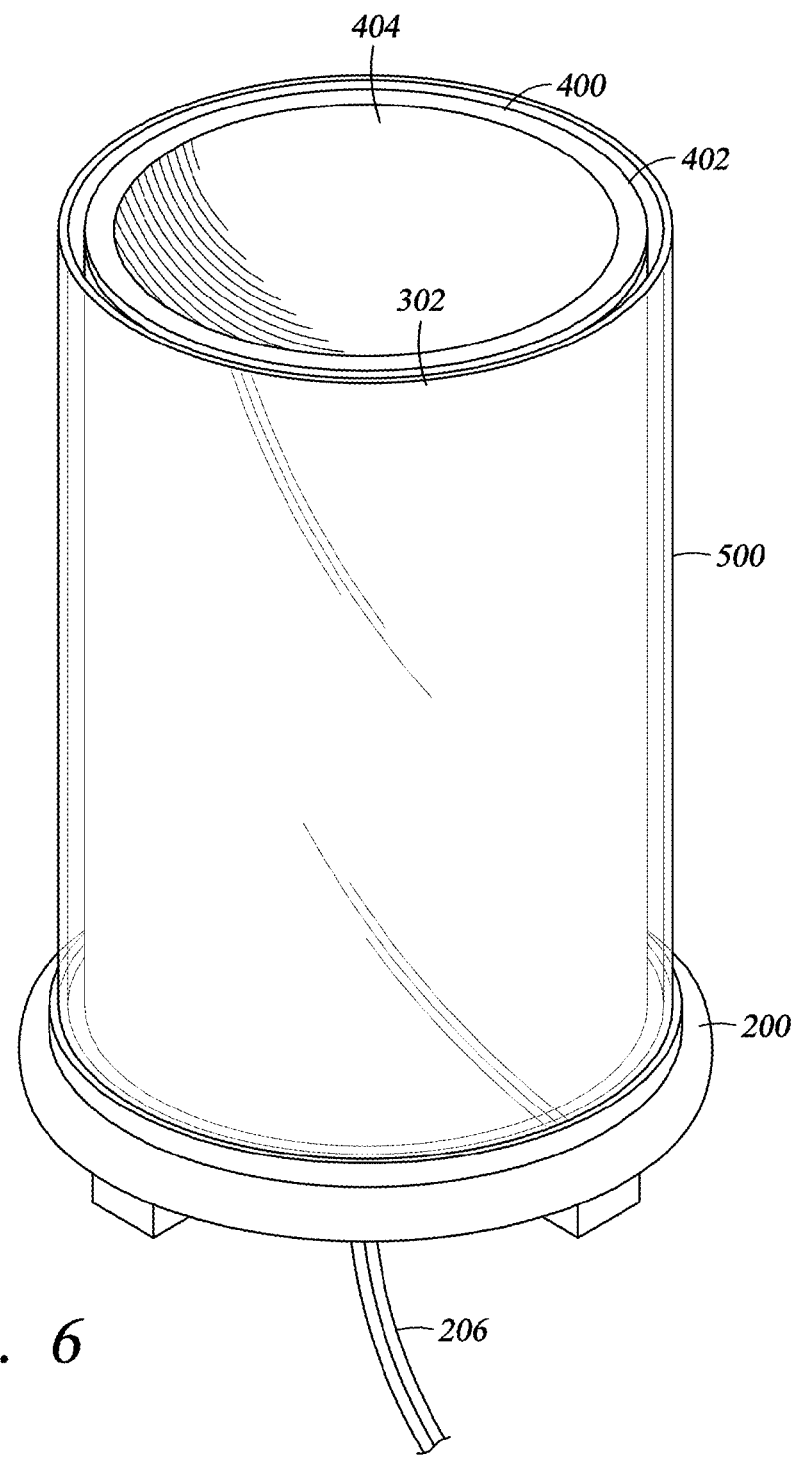
FIG. 6 is a perspective view of aspects of the fragrance diffuser.

The outer glass 500 includes a top edge 502 and a bottom edge 504. The outer glass 500 may be a cylinder, as shown in the illustrated embodiment, although other shapes may be used without departing from the present disclosure. For embodiments in which the outer glass 500 is a cylinder, the top edge 502 and the bottom edge 504 each have a diameter $D_2$, and the diameter $D_2$ is larger than the diameter $D_1$. The outer glass 500 is configured to be interchangeable and removable and when installed rests on the base 200, surrounding the inner glass 300. FIG. 6 illustrates the base 200 with the outer glass 500 surrounding the inner glass 300. As illustrated, an annular area is formed between the inner and outer glass.

The fragrance diffuser 100 also includes custom insert 600. The custom insert 600 may include one or more decorative images 602, such as a photograph collage, provided on a suitable material, such as paper or plastic. The user of the fragrance diffuser 100 may create or otherwise obtain any desired decorative images 602 for the custom insert 600. For example, the custom insert 600 may include printed photographs of cherished memories, loved ones, or calming scenery. As another example, the custom insert 600 may include a child's artwork. As another example, the custom insert 600 may include an abstract decorative pattern.

The custom insert 600 is sized and shaped to be placed in the annular area between the inner glass 300 and the outer glass 500. For example, for embodiments in which the inner glass 300 and the outer glass 500 are cylinders having diameters $D_1$ and $D_2$, respectively, the custom insert may have a length approximately between $\pi \times D_1$ and $\pi \times D_2$. Use of the fragrance diffuser 100 may include following instructions and/or a template to create a custom insert 600 of suitable dimensions. The custom insert 600 may be attached to the outer glass 500 by an adhesive, such as tape or glue.

Figure 7:
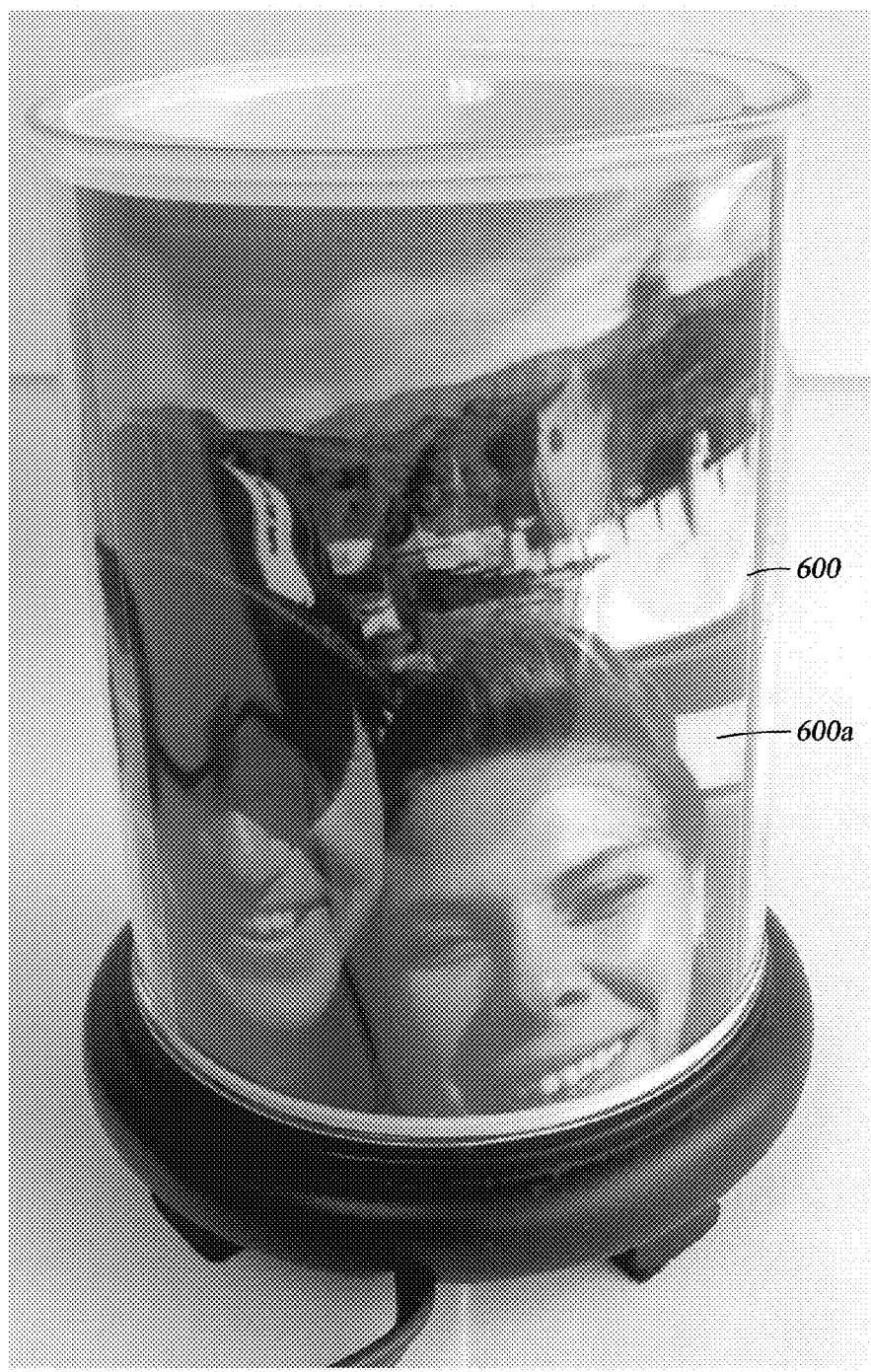
FIG. 7 is a perspective view of aspects of the fragrance diffuser.
Figure 8:
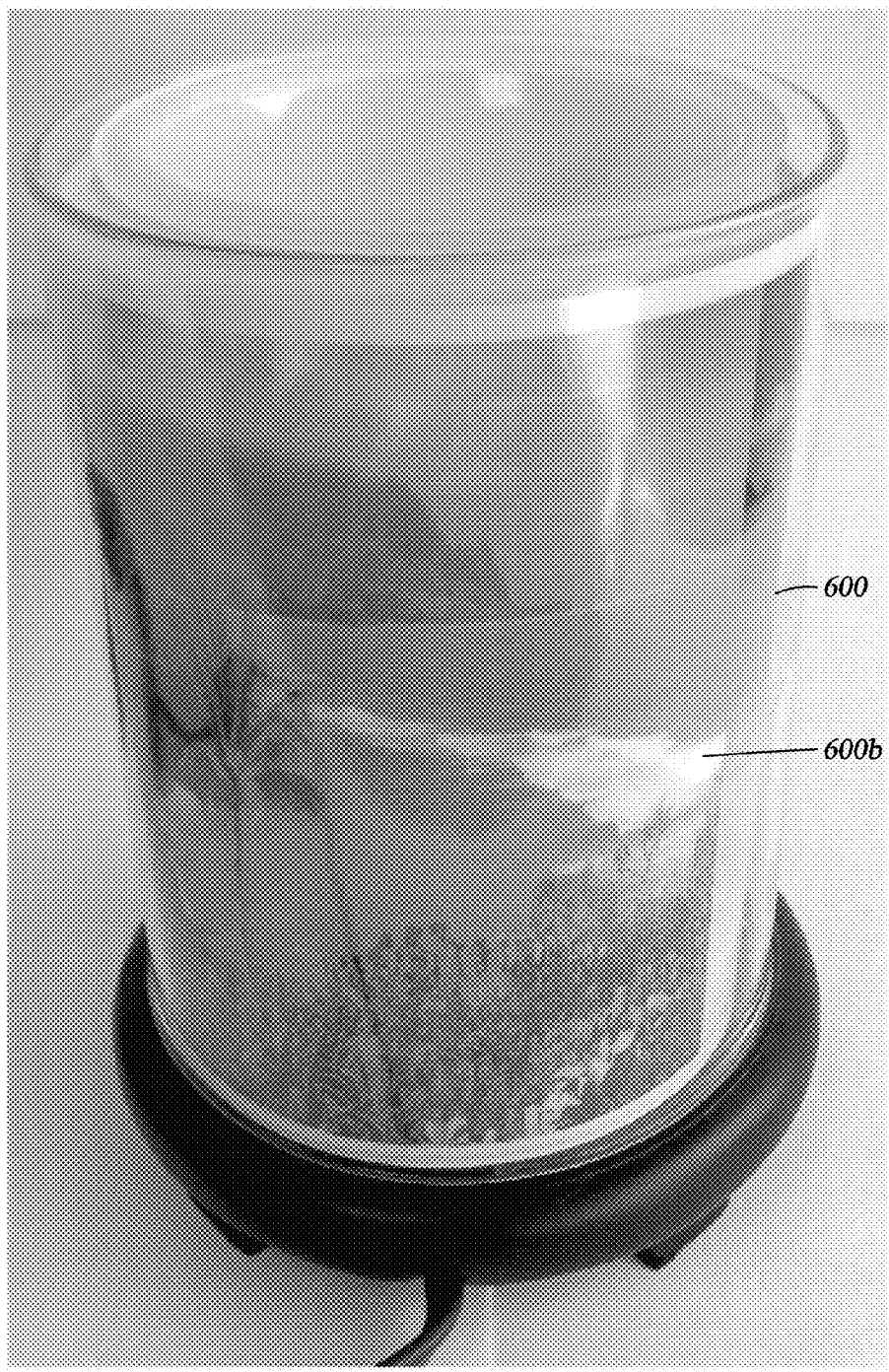
FIG. 8 is a perspective view of aspects of the fragrance diffuser.

FIGS. 7 and 8 illustrate the fragrance diffuser 100 with the custom insert 600 placed between the inner glass 300 and the outer glass 500. In FIG. 7, the custom insert 600 includes first decorative images 602a. In FIG. 8, the custom insert 600 includes second decorative images 602b. As can be seen, the user can readily change the custom insert 600 as desired, e.g., when a different décor is desired. Furthermore, the fragrance diffuser 100 can be highly personalized by using any desired decorative images 602 for the custom insert 600.

While the foregoing is directed to embodiments of the present invention, other and further embodiments of the invention may be devised without departing from the basic scope thereof, and the scope thereof is determined by the claims that follow.

The invention claimed is:

1. A decorative fragrance diffuser comprising:
a base;
a light source mounted to the base;
an inner member having an open bottom end disposed on the base such that the inner member surrounds the light source;
a cover disposed on an open upper end of the inner member that closes the open upper end, wherein the cover has a basin portion configured to support a fragrant element; and
an interchangeable outer member surrounding the inner member, wherein an annular area is formed between the inner member and the interchangeable outer member.

2. The decorative fragrance diffuser of claim 1, further including a custom insert located between the inner member and the interchangeable outer member.

3. The decorative fragrance diffuser of claim 2, wherein the interchangeable outer member is removable from surrounding the inner member.

4. The decorative fragrance diffuser of claim 3, wherein the interchangeable outer member is replaceable with another interchangeable outer member.

5. A method of using a decorative fragrance diffuser comprising:
providing a base and a light source mounted to the base;
surrounding the light source with an inner member having an open bottom end resting on the base;
closing an open upper end of the inner member with a cover that has a basin portion configured to support a fragrant element;
surrounding the inner member with an interchangeable outer member, thereby creating an annular area between the inner member and the interchangeable outer member; and
placing a custom insert between the inner member and the interchangeable outer member or including a decorative element on the interchangeable outer member.

6. The method according to claim 5, further comprising:
heating the fragrant element with heat from the light source.

7. The method according to claim 5, further comprising replacing the interchangeable outer member with a second, different interchangeable outer member.

8. The method according to claim 5, wherein the custom insert is created by following instructions or a template to create the custom insert with suitable dimensions.

9. The method according to claim 5, wherein at least one of the inner member and the interchangeable outer member is made of glass.

10. The method according to claim 5, wherein at least one of the inner member and the interchangeable outer member is transparent, colored, or textured.

11. The method according to claim 5, wherein the interchangeable outer member has an open bottom end that rests on the base.

12. The method according to claim 5, wherein the interchangeable outer member has a diameter greater than a diameter of the inner member.

13. The decorative fragrance diffuser of claim 1, wherein at least one of the inner member and the interchangeable outer member is made of glass.

14. The decorative fragrance diffuser of claim 1, wherein at least one of the inner member and the interchangeable outer member is transparent, colored, or textured.

15. The decorative fragrance diffuser of claim 1, wherein the interchangeable outer member has an open bottom end that rests on the base.

16. The decorative fragrance diffuser of claim 1, wherein the interchangeable outer member has a diameter greater than a diameter of the inner member.

* * * * *